(12) United States Patent
Frey et al.

(10) Patent No.: US 7,147,471 B2
(45) Date of Patent: Dec. 12, 2006

(54) USE OF MOULDING COMPOUNDS FOR PRODUCING TREATMENT DEVICES

(75) Inventors: Oliver Frey, Gauting-Königswiesen (DE); Roland Brem, Mering (DE)

(73) Assignee: 3M ESPE AG, Seefeld (DE)

( * ) Notice: Subject to any disclaimer, the term of this patent is extended or adjusted under 35 U.S.C. 154(b) by 329 days.

(21) Appl. No.: 10/433,895

(22) PCT Filed: Nov. 29, 2001

(86) PCT No.: PCT/EP01/13935

§ 371 (c)(1),
(2), (4) Date: Jun. 6, 2003

(87) PCT Pub. No.: WO02/45661

PCT Pub. Date: Jun. 13, 2002

(65) Prior Publication Data

US 2004/0042960 A1 Mar. 4, 2004

(30) Foreign Application Priority Data

Dec. 8, 2000 (DE) .............................. 100 61 195

(51) Int. Cl.
A61K 39/395 (2006.01)
A61K 49/00 (2006.01)
G01N 33/53 (2006.01)

(52) U.S. Cl. ................. 433/217.1; 424/9.1; 424/130.1

(58) Field of Classification Search ............... 600/300, 600/590; 424/433, 443, 130; 602/61, 62, 602/63, 901; 604/304, 308; 433/217.1
See application file for complete search history.

(56) References Cited

U.S. PATENT DOCUMENTS

| | | |
|---|---|---|
| 3,255,079 A | 6/1966 | Schroeder et al. |
| 3,309,274 A | 3/1967 | Brilliant |
| 3,453,242 A | 7/1969 | Schmitt et al. |
| 3,634,400 A | 1/1972 | Schmitt et al. |
| 3,897,376 A | 7/1975 | Lampe |
| 3,903,252 A | 9/1975 | Stearns et al. |
| 3,959,881 A | 6/1976 | Kokal, Jr. |
| 4,035,453 A | 7/1977 | Hittmair et al. |
| 4,093,555 A | 6/1978 | Schmitt et al. |
| 4,167,618 A | 9/1979 | Schmitt et al. |
| 4,302,439 A | 11/1981 | Selwyn |
| 4,368,272 A | 1/1983 | Kashket |
| 4,397,944 A | 8/1983 | Komura et al. |
| 4,459,277 A | 7/1984 | Kosti |
| 4,582,795 A | 4/1986 | Shibuya et al. |
| 4,666,700 A | 5/1987 | Frysh |
| 4,976,951 A | 12/1990 | Rosenburg et al. |
| 4,992,256 A | 2/1991 | Skaggs et al. |
| 5,190,743 A | 3/1993 | Simone et al. |
| 5,357,989 A | 10/1994 | Gathani |
| 5,395,239 A | 3/1995 | Komatsu et al. |
| 5,422,093 A | 6/1995 | Kennedy et al. |
| 5,563,124 A | 10/1996 | Damien et al. |
| 5,665,559 A | 9/1997 | Simonson |
| 5,725,373 A | 3/1998 | Yeh |
| 5,981,300 A | 11/1999 | Möll |
| 6,051,249 A * | 4/2000 | Samuelsen .................. 424/443 |
| 6,084,005 A | 7/2000 | Fukunishi et al. |
| 6,197,331 B1 * | 3/2001 | Lerner et al. ................ 424/448 |
| 6,699,040 B1 | 3/2004 | Hahn et al. |
| 6,860,879 B1 | 3/2005 | Irion et al. |

FOREIGN PATENT DOCUMENTS

| | | |
|---|---|---|
| DE | 914325 | 7/1954 |
| DE | 17445810 | 1/1970 |
| DE | 2515593 | 10/1975 |
| DE | 3741575 | 6/1988 |
| DE | 3743983 | 7/1988 |
| DE | 3838587 | 5/1990 |
| DE | 3939998 | 6/1991 |
| DE | 4306997 | 9/1994 |
| DE | 19719438 | 11/1997 |
| DE | 19714167 | 10/1998 |
| DE | 19827417 | 12/1999 |
| DE | 19942459 | 3/2001 |
| DE | 10018918 | 11/2001 |
| EP | 0110429 | 6/1984 |
| EP | 0231420 | 8/1987 |
| EP | 0268347 | 5/1988 |
| EP | 0304871 | 3/1989 |
| EP | 0321420 | 6/1989 |
| EP | 0480238 | 4/1992 |
| GB | 1044753 | 10/1966 |
| JP | 11-228597 | 8/1990 |

(Continued)

OTHER PUBLICATIONS

Kneist, S.; Klein, C.; Rupf, S.; Eschrich, K.—Quintessenz (1999) 50, 33-43.

(Continued)

Primary Examiner—Cris L. Rodriguez
Assistant Examiner—Candice C. Stokes
(74) Attorney, Agent, or Firm—Crowell & Moring LLP

(57) ABSTRACT

A method for treating hard tissue infection in a site-specific manner, comprising preparing a negative mold of the hard tissue using an impression material which contains a diagnostic additive which generates an identifiable signal on contact with infected tissue; applying a treatment agent to the negative mold at one or more of infected sites; and re-applying the negative mold on the originally molded hard tissue for a suitable period of time. Also disclosed are methods for making the negative mold, a mouthpiece corresponding to the negative mold, and a treatment device, as well as the treatment device and mouse piece so produced.

12 Claims, No Drawings

FOREIGN PATENT DOCUMENTS

| | | |
|---|---|---|
| JP | 4-299998 | 10/1992 |
| JP | 10-33576 | 2/1998 |
| JP | 11-14624 | 1/1999 |
| WO | WO 91/14000 | 9/1991 |
| WO | WO 94/12877 | 6/1994 |
| WO | WO 95/07286 | 3/1995 |
| WO | WO 96/07103 | 3/1996 |
| WO | WO 96/32647 | 10/1996 |
| WO | WO 98/21583 | 5/1998 |

OTHER PUBLICATIONS

Aass, A. M.; Preus, H. R., Zambon, J. J., Gjermo, P.—Scand J. Dent Res (1994) 102, 355-360.

Rupf, S.; Kneist, S.; Merte, K.; Eschrich, K.—Eur. J. Oral. Sci (1999) 107, 75-81.

J. Meyle—Deutsche Zahnärztliche Zeitschrift (1999) 54, 73-77.

O. C. Dermer, G. E. Ham—"Ethylenimine and other Aziridines" Academic Press (1969).

* cited by examiner

USE OF MOULDING COMPOUNDS FOR PRODUCING TREATMENT DEVICES

The present invention relates to a treatment device for applying treatment agents to infected hard tissue, with it being possible to produce the treatment device individually using an impression material which contains diagnostic additives.

The skilled person is familiar, for example from EP-A-0 304 871, with single-site tests which are based on individual samples being taken from defined points in the oral cavity, for example gingival pockets, tooth surfaces or tooth root canals. The subsequent analysis of these samples is carried out using methods which vary very widely, depending on the problem, with it being possible to differentiate four general approaches:

1. The microbiological diagnosis is frequently made after incubating the samples in suitable culture media for several days because the number of microorganisms which were originally present is not sufficient for a direct diagnosis. After the microorganisms have multiplied, the colony forming units (CFUs) are counted and conclusions are drawn with regard to the number of microorganisms present in the sample (Kneist, S.; Klein, C.; Rupf, S.; Eschrich, K. Quintessenz (1999) 50, 33–43). In these test systems, the live microorganisms which are present in the sample are able to multiply under optimal conditions. Consequently, the analytical result indicates what would be the maximum possible pathogenic potential of the evaluated microorganism if the microorganism, which was selectively propagated using defined culture media, were able to multiply in a similarly unhindered manner in the oral cavity.

However, as is well known, such optimal growth conditions certainly do not exist in the oral cavity, which means that the test result is only of limited informative value.

In addition to this, the fact must not be overlooked that incubating the samples creates a culture of pathogenic microorganisms which in practice have to be treated with the appropriate precautions in order to minimize risk. Special disposal is required. Apart from these disadvantages, the incubation methods for making a microbiological diagnosis are expensive and very time-consuming.

2. Immunological methods represent another general approach for collecting microbiological data in single-site tests. In this case, use is made of monoclonal or polyclonal antibodies which are directed against microorganism surface structures or substances which microorganisms secrete. In addition to this, it is also possible to use appropriate antibodies to monitor inflammatory processes, for example. WO-94/12877, U.S. Pat. No. 5,665,559, WO-96/07103 and WO-96/32647 may be mentioned as examples of this.

While the immunological methods in accordance with paragraph 2 are more specific, more rapid and more economical than the incubation methods in accordance with paragraph 1, they suffer from marked weaknesses in reproducibility which are determined, inter alia, by the sampling. For example, substantial quantities of dead microorganisms are present in a plaque region in addition to live microorganisms. The ratio between dead and live microorganisms may be different depending on the sampling. Since the antibodies are unable to distinguish between live and dead microorganisms, it follows that there is an unpredictable variation range in deducing the pathogenic potential of the evaluated microorganism which is present (Aass, A. M.; Preus, H. R., Zambon, J. J., Gjermo, P. Scand J. Dent Res (1994) 102, 355–360).

3. The method which has the highest sensitivity is based on the polymerase reaction technology (PCR). Very small quantities of microorganisms can be detected with a high degree of specificity. However, PCR technology is time-consuming, complex and costintensive. It is not a trivial matter to master it (Rupf, S.; Kneist, S.; Merte, K.; Eschrich, K. Eur. J. Oral. Sci (1999) 107, 75–81).

4. In addition, some methods which use biochemical markers for diagnosing stomatopathies have been described. The article by J. Meyle, Deutsche Zahnärztliche Zeitschrift (1999) 54, 73–77) provides a review. The informative value of the individual biochemical markers has to be assessed in a discriminating manner taking into account the clinical studies and is a matter for a skilled person. It should be emphasized that single-site methods are used to determine the biochemical markers. The reader is referred to patent specification WO-98/21583 as an example. The auxiliary tools which are required in this case are characterized by the fact that they bind the samples to be investigated (WO-91/14000, EP-A-0 304 871 and U.S. Pat. No. 5,725,373). A separate auxiliary tool must be used for each sampling site, and then analyzed individually.

In principle, all the single-site methods which are disclosed in the prior art suffer from the crucial disadvantage that it is only possible to obtain a description of the situation in the oral cavity which is approximately complete by taking a large number of individual samples. Paper tips, which are introduced into the gingival pockets or root canals, are frequently used for the sampling (U.S. Pat. No. 5,725,373 and EP-A-0 304 871).

It is known that periodontitis activity can vary greatly from gingival pocket to gingival pocket in a patient even though the periodontitis pathogens are present ubiquitously in the gingival pockets. For this reason, it is necessary to take, and analyze, substantially more than 25 individual samples in order to make a diagnosis, without being able to guarantee that there has been no failure to take into account one or other of the periodontitis foci.

From this, it becomes clear in principle that punctate recordings of numbers only permit unsatisfactory descriptions of the situation in the oral cavity. As a consequence, the high time and cost consumption of the single-site techniques can only be justified with qualifications. Single-site techniques have therefore not become accepted for broad application in oral cavity diagnostics.

There has therefore for a long time now been a need to have available a simple and inexpensive method for simultaneously making multiple and also site-specific and substance-specific diagnoses in the oral cavity.

This problem is addressed in DE-199 26 728. This patent application describes a moldable, hardenable or film-forming support material which contains additives which can be used diagnostically for making a site-specific and substance-specific intraoral diagnosis. The patent explains that these additives enable the skilled person to produce images for intraorally detecting pathogenic substances and/or microorganisms in a site-specific and substance-specific manner or for intraorally detecting, in a site-specific and substance-specific manner, substances which point to stomatopathies or healing processes.

DE-A-198 27 417 describes a film-forming material for differentially modifying the optical properties of different cells containing a basal material, such as an impression material, and a modifying substance, which is dispersed in this impression material, for use in periodontology. The patent reports that it is also possible to use the modifying material for the purposes of therapy. In this regard, it is explained that the modifying material is to be applied once again to the diseased sites. The diseased sites are identified by fluorescence directly at the interoral hard tissue. The diseased sites are treated by way of photodynamic therapy.

Taking the finding which was obtained using the support materials described in DE-199 26 728 as a basis, subsequent treatment of the infected regions has to take place, for example, by cleaning the infected regions and, following on from that, applying a treatment agent.

These subsequent treatments are relatively time-consuming and frequently not sufficiently effective, and also wasteful of materials since the sites to be treated, as described in DE-A-198 27 417, are not initially known.

It is consequently an object of the present invention to provide a treatment device which makes it possible to treat the infected regions more effectively.

This object is achieved by using support materials, which contain additives which can be used diagnostically for site-specific and substance-specific diagnosis, for producing a negative mold in a method for treating infected hard tissue.

The invention also relates to the corresponding treatment device itself and to a method for producing it.

The presence of the diagnostic additives makes it possible to intraorally detect pathogenic substances and/or microorganisms in a site-specific and substance-specific manner or to intraorally detect, in a site-specific and substance-specific manner, substances which point to stomatopathies or healing processes.

Using this information as a basis, the present invention makes it possible to provide a treatment device for the site-specific treatment of the infected regions of the hard tissue.

In this connection, "site-specific" is to be understood as meaning, within the sense of the invention, the selective treatment of the infected regions, with the aim being to avoid uninfected tissue coming into contact with the treatment agent, something which can in fact be achieved by selecting suitable treatment agents.

In this way, the quantity of treatment agent can be restricted to the necessary minimum, thereby making it possible to economize on costs. Another crucial point is that the stress on the patient, as regards the quantity of the treatment agent employed which is acting on the patient, and the time for which it acts, can be drastically reduced.

It is also advantageous not only that using the support materials makes it possible to describe the situation of the individual teeth virtually completely, while processing a large number of individual samples, and to archive the current clinical picture, but also that the treatment device makes it possible to treat the infected tissue synchronously in a site-specific manner. In addition to occlusal masticatory surfaces and vestibular, lingual, coronal, apical, cervical, gingival and incisal regions of a tooth, the delineation acuities of the support materials also record the interproximal regions between the teeth.

The terms "comprise" or "contain" introduce enumeration of features. The fact that the word "a" is used before mentioning a feature in the claims does not rule out the possibility that said features may be present several times, in the sense of "at least one".

Within the sense of the invention, the term "support material" is to be understood as meaning any moldable, hardenable or film-forming support material, in particular for intraoral use.

Examples of suitable support materials are dental impression materials or films, in each case on a silicone, polyether-silicone, polyether, alginate or hydrocolloid basis. Alginates, preferably without any addition of phosphates or pyrophosphates, are used for a number of areas of application, such as caries diagnosis. Other known synthetic materials, such as polyethylenes, polypropylenes, poly(meth)acrylates, polymethanes, polycarbonates, polysulfide, polyvinyl chlorides or rubber, are also suitable for use as support materials. In addition to this, hydrogels, for example on a polyvinylpyrrolidone or polyvinyl alcohol basis, are suitable for use as support materials. Dental gypsum preparations, noncurable kneadable substances, such as plasticines or solid dispersions in liquids, for example pastes and similar substances composed of silicone, waxes, gelatin, starch, fats and the abovementioned support materials, are likewise suitable for implementing the methods according to the invention.

Addition crosslinking or condensation crosslinking silicones, polyether-silicones or polyethers form the basis for many impression materials. These materials have been described in detail in the prior art, such that there is no need to deal with them in any detail here. Addition crosslinking or condensation crosslinking silicones are described, for example, in U.S. Pat. No. 3,897,376, in EP-B-0 231 420 and in U.S. Pat. No. 4,035,453, which is mentioned on page 3 in EP-B-0 321 420, and, furthermore, in EP-A-0 480 238 (see, in particular, page 2, lines 3–26) and in EP-B-0 268 347. The disclosure of these documents is incorporated herein by reference. Polyether-silicones are described, inter alia, in DE-A-37 41 575 and DE-A-38 38 587, the disclosure of which documents is likewise incorporated herein by reference. Polyethers are described, for example, in DE-B-17 45 810, DE-A-43 06 997, DE-A-40 93 555, DE-C-25 15 593, DE-A-197 19 438 and U.S. Pat. No. 3,453,242, the disclosure of which documents is likewise incorporated herein by reference.

Support materials based on polyether are particularly suitable. In this connection, the substances comprise the following constituents, for example:

(A) from 30 to 97, preferably from 40 to 89, particularly preferably from 40 to 80.5, % by weight of at least one N-alkylaziridinopolyether having molar masses in the range from 1000 to 20 000 g/mol and aziridino equivalent masses in the range from 500 to 8000 g/equivalent, (B) from 1 to 10, preferably from 1 to 5, particularly preferably from 1.5 to 3, % by weight of initiator substances which are suitable for effecting the hardening of the N-alkylaziridinopolyethers, (C) from 1 to 50, preferably from 5 to 45, particularly preferably from 8 to 43, % by weight of organic diluents, (D) from 1 to 50, preferably from 5 to 40, particularly preferably from 10 to 30, % by weight of modifiers, including fillers, dyes, pigments, thixotropic agents, flow improvers, polymeric thickeners, surface-active substances, odiferous substances and flavorings, (E) from 0.0001 to 10% by weight, preferably from 0.01 to 1% by weight, of diagnostic additives.

Constituent (A) comprises N-alkylaziridinopolyethers, with it being possible for the polyether parent substances to be homopolymers composed of ethylene oxide, propylene oxide or tetrahydrofuran, random copolymers and terpolymers of said monomers and/or block copolymers composed of ethylene oxide and propylene oxide.

Those initiator substances in accordance with constituent (B) which enable the mixed preparation to be cured to give an elastic solid in a time interval of from 1 to 20 minutes, with this solid meeting the demands placed on an elastic impression material in accordance with DIN/EN 2482 and possessing a Shore A hardness (DIN 53505) of at least 20 after 24 hours of storage, are suitable for use in two-component impression materials.

Many of the known initiators can be used as initiators of the catalyst component. Use is expediently made of those initiators or initiator systems which permit the course of the curing to be easily regulated, which do not produce any side effects and which make it possible to reproducibly achieve the requisite level of the mechanical properties.

DE-C-914 325 proposes that oxonium salts, ammonium salts and sulfonium salts be used as initiator substances.

O. C. DERMER, G. E. HAM, "Ethylenimine and other Aziridines" Academic Press (1969) contains a comprehensive account of the initiator substances which are used for curing N-alkylaziridino compounds.

According to this publication, a large number of compound classes and compounds have been found to be polymerization initiators which are suitable in principle. However, it is very difficult, in the practical application of the cationic polymerization of aziridinopolyethers, to establish the desired course of curing, giving a sufficiently long working time and rapid final curing. This aim can be achieved by using special trisalkylsulfonium salts, as are described, for example, in EP-A-0 110 429.

In principle, the criteria of the hardening rate and the properties of the elastic solid can be achieved using special trisalkylsulfonium salts.

Patent application DE-100 18 918 describes initiators which only impart a small degree of acidity to the catalytic component and which make it possible to achieve a readily adjustable, relatively long working time after the basal component and the catalytic component have been mixed.

Initiator systems of this type are suitable for curing the basal pastes at the requisite rate. Using them makes it possible to achieve the desired properties of the elastic solid.

Patent application DE-19942459 describes elastomeric substances which contain an improved catalytic component and which are characterized by an increased degree of extensibility. This invention uses boric acid complexes as initiators. These initiators have proved to be of particular value for curing the N-alkylaziridinopolyethers.

Polyetherpolyols, such as polypropylene glycols or mixed polyetherols containing tetrahydrofuran units and/or ethylene oxide units and/or propylene oxide units, polyesterpolyols, such as polycaprolactonediols and polycaprolactonetriols, polycarbonatediols, aliphatic esters, oils, fats, waxes, aliphatic hydrocarbons, araliphatic hydrocarbons, and also monofunctional or polyfunctional esters of polybasic acids, such as phthalic acid or citric acid, or esters or amides of alkylsulfonic acids and arylsulfonic acids, are used as the organic diluent in accordance with constituent (C).

The modifiers in accordance with constituent (D) are for the most part finely divided fillers, such as aluminum silicates, precipitated silicic acids, quartz powder, wollastonite, mica powder and diatomaceous earth, and also dyes and pigments whose addition makes it easier to assess mixing efficiency and reduces the danger of any possible confusion, thixotropic agents, such as finely dispersed silicic acids and other additives influencing flow behavior, such as polymeric thickeners, and, in addition, surface-active substances for regulating initial flow behavior, and also odiferous substances and flavorings.

A polymerizable liquid or a solution of a polymeric substance which is sprayed or applied, for example painted, onto the sites to be investigated, can also be another possible support material. These substances are typically nitrocellulose-based lacquers containing a volatile solvent and, where appropriate, other auxiliary substances which cure to form a solid layer which can be stripped off after the substrate has taken up the marker compound. In general, it is possible to use any polymers which can be taken up in suitable, readily volatile solvents. It is known, for example, to use polyurethanes in acetone. Suitable film-forming systems are sufficiently well known from dye and lacquer chemistry.

Without the following enumeration being understood as being limiting for the present invention, examples of diagnostic additives are:

dye indicators, for example pH indicators, such as bromophenol blue, congo red, bromocresol green, oregon green derivatives, rhodol derivatives, redox indicators, such as methylene blue, 5-cyano-2,3-ditolyl tetrazolium chloride (CTC), 2-(4-iodophenyl)-3-(4-nitophenyl)-5-phenyl-2H-tetrazolium chloride (INT), 8-dimethylamino-2,3-benozophenoxazine (meldola's blue), 1-methoxyphenazine methosulfate (MPMS), 5-(3-carboxymethoxyphenyl)-2-(4,5-dimethylthiazolyl)-3-(4-sulfophenyl) teratzolium (MTS), 3-(4,5-dimethylthiazol-2-yl)-2,5-diphenyltetrazolim bromide (MTT), 3,3'-(3,3'-dimethoxy-4,4'-biphenylene-bis [2-(4-nitrophenyl-5-phenyl)]-2 H-tetrazolium chloride (NBT), nitrotetrazolium violet (NTV), phenazine methosulfate (PMS), sodium 3'-[1-[(phenylamino)carbonyl]-3,4-tetrazolium [bis (4-methoxy-6-nitro)benzenesulfonic acid (XTT), phenazine ethosulfate (PES) and WST-1)

fluorescent indicators, for example oregon green 488 BAPTA, calcium green, calcium orange and calcium crimson, chemoluminescent indicators, vital indicators, for example 5-bromo-2'-deoxyuridine, other dye indicators, for example p-nitroaniline derivatives, 2-naphthylamine derivatives, 7-amino-4-methylcoumarine derivatives, 7-amino-4-chloromethylcoumarin derivatives, 6-aminoquinoline derivatives, rhodamine derivatives, 5,5'-dithiobis(2-nitrobenzoic acid), monobromobimane derivatives, tetramethylrhodamine derivatives, eosin derivatives, erythrosine derivatives, Texas red derivatives, coumarine derivatives, pyridyloxauzole derivatives, benzofurazan derivatives, naphthalene derivatives, didansyl cysteine, dansyl derivatives, aziridine derivatives, pyrene derivatives and Coomassie blue).

In addition to this, the indicator substances can, for example, be covalently bonded to enzymes, proteins, glycoproteins, lipopolysaccharides, polysaccharides, polyclonal and monoclonal antibodies, DNA, RNA, cell organelles or microorganisms.

"Diagnostic additives" are also understood as meaning antibodies which are directed against marker compounds, and also polyclonal antibodies and their subclasses, and also monoclonal antibodies. In addition to this, the antibodies can, for example, be covalently bonded to enzymes, proteins, glycoproteins, lipopolysaccharides, polysaccharides, DNA, RNA, cell organelle, microorganisms or other support materials.

Diagnostic additives can be enzymes of the following classes, with the following enumeration being by way of example and not limiting for the invention:

oxidoreductases and their subclasses, for example dehydrogenases, such as lactate dehydrogenase, oxidases, peroxidases, reductases, monooxygenases and dioxygenases;

transferases and their subclasses, for example $C_1$-transferases, glycosyltransferases, such as glusoyltransferases, fructosyltransferases, aminotransferases and phosphotransferases;

hydrolases and their subclasses, for example esterases, glycosidases, such as glucanase and fructanase, peptidases, for example dipeptidylpeptidases, Arg-gingipain, Lys-gingipain, collagenases, gelatinases, cathepsins, elastase and amidases, lyases and their subclasses, for example C—C-lyases, C—O-lyases, C—N-lyases and C—S-lyases;

isomerases and their subclasses, for example epimerases, cis-trans isomerases and intramolecular transferases;

ligases and their subclasses, for example C—C-ligases, C—O-ligases, C—N-ligases and C—S-ligases.

Nowadays, more than 2000 different enzymes are known. A system which takes into account action specificity and substrate specificity was developed for classifying them. It follows from this that specific substrates and/or coenzymes (NAD(P), NAD(P)H, FAD, FMN, lipoamide, ubiquinone, heme, ATP, ADP, AMP, GTP, GDP, GMP, UTP, UDP, UMP, CTP, CDP, CMP, coenzyme A, thiamine diphosphate, pyridoxal phosphate, biotin, tetrahydrofolate belong to each enzyme. These specific substrates and/or coenzymes have to be present, as diagnostic additives, if, for example, one or more enzymes is/are used as marker substance(s). Conversely, it is naturally the case that specific enzymes can be used as diagnostic additives when specific substrates, for example sugar phosphates, lactic acid/lactate, pyruvate, acetic acid/acetate, propionic acid/propionate, formic acid/formate, peptides or synthetic peptides are used as marker substances.

In addition to this, the enzymes can be bonded covalently to a support material.

Diagnostic additives can also be those substances which have to be concomitantly present in order to be able to diagnose the marker substances. Such substances include:

buffering substances, for example sodium phosphate, sodium hydrogen phosphate, sodium dihydrogen phosphate, potassium phosphate, potassium hydrogen phosphate, potassium dihydrogen phosphate, sodium pyrophosphate, sodium carbonate, potassium carbonate, sodium hydrogen carbonate, potassium hydrogen carbonate, sodium tetraborate, acetic acid/acetate, citric acid/citrate, diethylbarbituric acid, tris(hydroxymethyl)aminomethane (TRIS), glycine, glycylglycine, N-(2-acetamido)-2-aminoethanesulfonic acid (ACES), N-(2-acetamido)iminodiacetate (ADA), N,N-bis(2-hydroxyethyl)-2-aminoethanesulfonic acid (BES), N,N-bis(2-hydroxyethyl)glycine (BICINE), 2,2-bis(hydroxyethyl)iminotris(hydroxymethyl)methane (BIS-TRIS), 2-(cyclohexylamino)ethanesulfonic acid (CHES), 2-[4-(2-hydroxyethyl-1-piperazine)]ethanesulfonic acid (HEPES), 3-[4-(2-hydroxyethyl-piperazinyl)]propanesulfonic acid (HEPPS), 2-morpholinoethanesulfonic acid (MES), 3-morpholinopropanesulfonic acid (MOPS), piperazine-1,4-bis(2-ethanesulfonic acid) (PIPES), N-[tris(hydroxymethyl)methyl]-2-aminoethanesulfonic acid (TES) and N-[tris(hydroxymethyl)methyl]glycine (TRICINE);

acids, for example sulfuric acid, sulfurous acid, phosphoric acid, hydrochloric acid, acetic acid and nitric acid;

bases, for example sodium hydroxide, potassium hydroxide, lithium hydroxide, ammonia, calcium hydroxide and magnesium oxide;

solvents, for example water, methanol, ethanol, isopropanol, propanol, glycerol, dimethyl sulfoxide, tetrahydrofuran, acetone, butanone, cyclohexane, toluene, methylene chloride, chloroform, alkanes and ethyl acetate;

salts, for example magnesium chloride, magnesium sulfate, magnesium nitrate, calcium chloride, calcium sulfate, calcium nitrate, iron(III) chloride, iron(II) chloride, zinc chloride, zinc sulfate, nickel chloride, manganese chloride, ammonium sulfate, sodium sulfate, sodium chloride, potassium chloride, sodium phosphates and potassium phosphates;

other substances, for example glutathione, bovine serum albumin, sucrose, glucose, fructose, trehalose, polyethylene glycols, polyvinylpyrrolidones and hydrogen peroxide.

In a special embodiment of the invention, the diagnostic additives can be present in microencapsulated form. A large number of molecules of diagnostic additives can be enclosed in a microcapsule. The potentiating effect which occurs is of particular advantage when using microencapsulated diagnostic substances.

In a quite general manner, when multicomponent diagnostic systems according to the invention, that is systems in which the necessary constituents for the detection are stored in several components, are used, the individual components can be present separated from each other, but in each case enclosed in microcapsules, or else partially microencapsulated and partially present in free form. It is naturally also possible, in the case of diagnostic systems containing more than two components, to keep at least two components in each case microencapsulated and at least one other component freely available in the support material. In each case, the only thing which is essential is that a reaction of the diagnostic additives, to give the desired end product, is prevented by the individual components being kept separate until one reaction partner is released by the microcapsule wall being destroyed.

Since impression materials are usually offered in two-component form, it can be advantageous to keep different components of the active compounds, microencapsulated or free, in different components of the impression materials, namely the basal paste and the catalyst paste.

In general, when selecting suitable support materials, care must be taken to ensure that these materials are compatible with the diagnostic substances. For example, when using fluorescent dyes, the support materials should naturally not contain any constituents which themselves fluoresce in the relevant wavelength range. The requirement for inert support materials within the sense of the diagnostic objective is a trivial matter for the skilled person, who can take account of it without difficulty.

Some of the diagnostically usable additives which are employed are commercially available and can, where appropriate, be modified physically, chemically, biochemically or recombinantly, with this being the case, in particular, for enzymes and their substrates, for antibodies and their antigens and for oligonucleotides and polynucleotides.

Within the sense of the invention, the term "identifiable signal" is to be understood as meaning any detectable signal. This includes, for example, color signals, for example fluorescent signals, UV signals, VIS signals, phosphorescent signals or luminescent signals which have, where appropriate, to be detected using a suitable device. In the same way, use of the methods according to the invention can generate signals which can be perceived by means of thermography, spectroscopy or chromatography or else by analyzing the topographical changes in the support materials. Preference is given to signals which can be optically recorded by the human eye.

Within the meaning of the invention, the term "negative mold" is to be understood as meaning the mold which is obtained when the cured impression material is lifted off the hard tissue or a corresponding model of the hard tissue. This negative mold can be the imprint of an entire upper or lower jaw or only isolated regions thereof. The term also includes the negative molds which have been produced while in the meantime preparing a positive mold using the negative mold which was initially prepared.

The following are mentioned as examples of pathogenic substances and/or microorganisms which are to be detected or of substances which are to be detected and which point to stomatopathies or healing processes or which lead or contribute to the formation of infected hard tissue within the meaning of the invention:

1. Metabolic products of bacteria, viruses or fungi, for example antigens, lipids, proteins, peptides, polysaccharides, DNA, RNA, sugar, amino acids, carboxylic acids, for example lactic acid and propionic acid, and also other low molecular weight, anionic, cationic or neutral substances and also their combinations which arise, for example, from ionic, polar, nonpolar, hydrophobic, covalent or adhesive interactions.

2. Surface structures of bacteria, viruses or fungi, which are composed, for example, of antigens, lipids, proteins, peptides, polysaccharides, DNA, RNA, sugars, amino acids or other low molecular weight, anionic, cationic or neutral substances, and also their combinations which arise, for example, from ionic, polar, nonpolar, hydrophobic, covalent or adhesive interactions.

3. Human or animal substances which are formed as a response to infections with bacteria, viruses or fungi and which comprise, for example, antibodies, antigens, lipids, proteins, peptides, polysaccharides, DNA, RNA, sugars, amino acids or other low molecular weight, anionic, cationic or neutral substances and also their combinations which arise, for example, from ionic, polar, nonpolar, hydrophobic, covalent or adhesive interactions.

4. Human or animal substances which point to stomatopathies and which are not based a priori on an infection with bacteria, viruses or fingi (for example cancer diseases), and which comprise, for example, antibodies, antigens, lipids, proteins, peptides, polysaccharides, DNA, RNA, sugars, amino acids or other low molecular weight, anionic, cationic or neutral substances and also their combinations which arise, for example, from ionic, polar, nonpolar, hydrophobic, covalent or adhesive interactions.

5. Substances which are present in structures which are known to be the consequence of, or the prerequisite for, the development of stomatopathies, for example plaque or biofilm, and which comprise, for example, antibodies, antigens, lipids, proteins, peptides, polysaccharides, DNA, RNA, sugars, amino acids or other low molecular weight, anionic, cationic or neutral substances and also their combinations which arise, for example, from ionic, polar, nonpolar, hydrophobic, covalent or adhesive interactions.

6. Substances which point to current healing processes which are known to be the consequence of stomatopathies or injuries, for example tissue and/or bone regeneration, and which comprise, for example, antibodies, antigens, lipids, proteins, peptides, polysaccharides, DNA, RNA, sugars, amino acids or other low molecular weight, anionic, cationic or neutral substances and also their combinations which arise, for example, from ionic, polar, nonpolar, hydrophobic, covalent or adhesive interactions.

The stomatopathies which can be diagnosed and treated also include caries, early onset periodontitis, prepubital periodontitis, juvenile periodontitis, rapidly progressing progressive periodontitis (RPP), adult periodontitis, refractory periodontitis, gingivitis, halitosis, infections with *Candida albicans*, *Candida krusei*, *Candida glabrata*, *Candida lusitaniae* and *Candida dubliniensis*, and cancer.

The different forms of the periodontitis which can be treated using the treatment device according to the invention are causally associated with infection with *Actinobacillus actinomycetemcomitans*, *Bacterioides forsythus*, *Campylobacter rectus*, *Capnocytophage ochracea*, *Capnocytophage gingivalis*, *Eikenella corrodens*, *Fusobacterium nucleatum*, *Porphyromonas asaccharolyticus*, *Porphyromonas gingivalis*, *Prevotella dentalis*, *Prevotella intermedia*, *Prevoltella nigrescens* and *Treponema denticola*. The presence and quantity of the bacteria in the sulcus liquid can be determined by using the impression materials. Specific polyclonal antibodies and their subclasses, or monoclonal antibodies, which are directed against surface antigens of these bacteria, for example fimbriae, extracellular polysaccharides or adhesins, are suitable for this purpose.

Caries is causally associated with infection with *Streptococcus salivarius salivarius*, *Streptococcus vestibularis*, *Streptococcus thermophilus*, *Streptococcus mutans*, *Streptococcus rattus*, *Streptococcus sobrinus*, *Streptococcus cricetus*, *Streptococcus downei*, *Streptococcus macacae*, *Streptococcus ferus*, *Streptococcus milleri*, *Streptococcus anginosus*, *Streptococcus constellatus*, *Streptococcus intermedius*, *Streptococcus mitis*, *Streptococcus oralis*, *Streptococcus sanguis*, *Streptococcus gordonii*, *Streptococcus parasanguis*, *Streptococcus crista*, *Streptococcus mitior*, *Lactobacillus acidophilus*, *Lactobacillus alimentarius*, *Lactobacillus brevis*, *Lactobacillus buchneri*, *Lactobacillus casei*, *Lactobacillus paracasei ss paracasei*, *Lactobacillus paracasei ss rhamnosus*, *Lactobacillus paracasei ss tolerans*, *Lactobacillus delbrueckii*, *Lactobacillus delbrueckii ss lactis*, *Lactobacillus delbrueckii ss delbrueckii*, *Lactobacillus delbrueckii ss bulgaricus*, *Lactobacillus endocarditis*, *Lactobacillus fermentum*, *Lactobacillus gasseri*, *Lactobacillus pseudoplantarum*, *Lactobacillus rhamnosus*, *Lactobacillus salivarius*, *Actinomyces israelii*, *Actinomyces odontolyticus*, *Actinomyces actinomycetemcomitans*, *Eikenella*, *Branhamella catarrhalis*, *Veillonella alcalescens*, *Veillonella parvula*, *Actinomyces naeslundii* and *Rothia dentocariosa*. As a result of using the impression materials, it is possible with polyclonal antibodies and their subclasses, or monoclonal antibodies, which are directed against various surface antigens of these bacteria, for example proteins, lipopolysaccharides, glycoproteins, fimbriae, extracellular polysaccharides, adhesions, lipoteichoic acid derivatives, glucan-binding proteins and collagen-binding proteins. The presence and quantity of the cariogenic bacteria are diagnosed and, based on that, a suitable treatment agent are applied to the negative mold.

Within the sense of the invention, the term "treatment agent" is in principle to be understood as meaning any agents which are suitable, when using the impression material containing diagnostic additives, for treating infections which are detected with these additives.

Suitable treatment agents include: fluoridating agents, such as fluoridating lacquers or gels, antibiotics, bacteriostatic agents and/or bactericides, such as chlorhexidine in the form of lacquers or gels, and also triclosan, quaternary ammonium compounds and mineral mixtures which enable the hard tooth substance to be efficiently remineralized.

Within the sense of the invention, the term "pretreated" is to be understood as meaning any way of modifying the surface. These ways include, in particular, mechanical pretreatments, for example by means of partially abrading or roughening the surface. However, the application of a chemical substance or a substance mixture is also included.

The abrading can be effected using scalpels, scissors or other cutting devices known to a person ordinarily skilled in dentistry.

The treatment device according to the invention normally comprises an impression spoon and a negative mold which is present in the spoon and which is composed of a support material containing diagnostic additives. A treatment agent is applied to this negative mold at at least one site.

This treatment device is then placed once again on the originally molded hard tissue for a given period of time.

Determined by how and where the treatment agent was applied to the negative mold, this treatment agent is now located, in a site-specific manner, at the infected sites of the hard tissue.

In this way, the treatment device according to the invention enables treatment agents to be used effectively. On the one hand effectively because only the required quantity of treatment agent is applied and on the other hand effectively because the treatment agent is only applied to the sites where treatment is required.

The invention additionally exhibits the following advantages: the person carrying out the treatment can treat the diseased or infected hard tooth substance regions more rapidly than previously because, when using the present invention, he is able to attend to several affected sites simultaneously and not, as previously, one after the other. This thereby also minimizes the stress for the patient and, finally, economizes on treatment costs.

As a result of using the support materials, it is possible to measure, in the sulcus liquid, enzyme activities which provide an indication of the presence and metabolic activity of a bacterium or a group of said bacteria. Diagnostic use is made of trypsin-like protease activity, preferably dipeptidylpeptidase activity, particularly preferably Arg-gingipain activity and Lys-gingipain activity. In order to determine Arg-gingipain activity, it is possible to use synthetic peptides which contain at least one Arg residue (in the P1 position) in addition to the detectable leaving group. In order to determine the Lys-gingipain activity, it is possible to use synthetic peptides which contain at least one Lys residue (in the P1 position) in addition to the detectable leaving group. In addition to p-nitroaniline derivatives, for example Nα-benzoyl-DL-arginine-p-nitroanilide, and 2-naphthylamine peptide derivatives, for example Na-benzoyl-DL-arginine-β-naphthylamide, it is possible to use 6-aminoquinoline peptide derivatives, rhodamine peptide derivatives and coumarin peptide derivatives, for example 7-amido-4-methylcoumarin, as N-t-Boc-Val-Pro-Arg-7-amido-4-methylcoumarin, and 7-amino-4-chloromethylcoumarin, as N-t-Boc-Val-Pro-Arg-7-amido-4-chloromethylcoumarin, as detectable leaving groups.

As a result of using the support materials, it is possible to employ polyclonal antibodies and their subclasses, or monoclonal antibodies, to diagnose the bacterial substances which lead to induction of cytokines. Preference is given to antibodies directed against lipopolysaccharides, lipoarabinomannans, peptidoglycans, teichoic acid derivatives, extracellular polysaccharides and lipid A.

As a result of using the support materials, it is possible to employ polyclonal antibodies and their subclasses, or monoclonal antibodies, to diagnose the cytokinin formation which is induced by periodontitis pathogens. It is possible to use antibodies which are directed against the interleukins IL-1, IL-2, IL-3, IL-4, IL-5, IL-6, IL-7 and IL-8, tumor necrosis factor TNFα, interferons α, β and γ, M-CSF colony-forming factors, growth factors EGF and TGFα, and MCP chemokines.

As a result of using support materials, it is possible to diagnose destruction of periodontal tissue by way of the enzyme activities of alkaline phosphatase, arylsulfatase, aspartate aminotransferase, β-glucuronidase, cathepsins (G, B and D), elastase, hyaluronidase, lactate dehydrogenase, lysozyme, matrix metalloproteinases (collagenases and gelatinases), tissue inhibitor metalloproteinases (TIMPs), stromelysin, lactoferrin, tryptase and myeloperoxidase.

As a result of using the support materials, it is possible to employ polyclonal antibodies and their subclasses, or monoclonal antibodies, to diagnose the molecular markers for gingivitis. These include cytokines, for example interleukins IL-1, IL-2, IL-4 and IL-6, TNFα and arachidonic acid derivatives, for example prostaglandin $E_2$.

As a result of using the support materials, it is possible to diagnose extracellular enzyme activities of cariogenic bacteria, for example proteases, preferably glucosyl transferases, glucanase, fructosyl transferase and fructanase.

As a result of using the support materials, it is possible to diagnose metabolic products of cariogenic bacteria, for example butyric acid, formic acid, preferably acetic acid, propionic acid, particularly preferably lactic acid. In addition, the acidification of the surrounding medium which accompanies the release of acid can be detected using pH indicators, for example using bromophenol blue, congo red, bromocresol blue, preferably rhodol derivatives, particularly preferably Oregon green derivatives. As a consequence of the acidification of the pH in the surrounding medium, such as plaque, calcium ions are dissolved out of the hard tooth substance. By using the impression material, it is possible to diagnose this process employing calcium indicators, for example calcium crimson, preferably calcium green, calcium orange or, particularly preferably, calcium Oregon green 488 BAPTA.

As a result of using the support materials, the increase or the decrease of the abovementioned marker compounds can be employed as a measure of the healing process.

It is surprising that, despite the dynamic processes which take place in the oral cavity, which is subject to a continuous exchange of liquids due to the secretions of the salivary glands and the sulcus liquid, sufficiently high concentrations of marker compounds are obtained on the surfaces of the support materials according to the invention, or in the support materials, to enable a reliable diagnosis to be made even within the context of routine treatments.

It is advantageous that, by using the impression material, it is possible to obtain a description of the situation in the oral cavity which is virtually complete, while processing a large number of individual samples, and to archive the current clinical picture. The use of addition-crosslinking silicone impression materials is of particular interest in this connection since the imprints can be kept for an almost unlimited period of time.

In a preferred embodiment, the support material contains at least one component, or else, for simplifying the diagnostic procedure, all the necessary components of the diagnostic test system. These diagnostic additives can, for example, be fixed locally on or in the support material by way of ionic, polar, nonpolar or hydrophobic interactions. It is also possible to fix diagnostic additives locally by firstly fixing the diagnostic additives to high molecular weight supports and then kneading them into the support substance. This thereby regulates the diffusion movement of the diagnostic additives in the support material. The formation of microstructures and/or microspaces in the support materials, for example in the form of foams, can assist the uptake and fixing of the components. The components can either be freely available in the support materials according to the invention or be present in another phase.

While the support materials generally contain from 0.0001 to 10% by weight, preferably from 0.01 to 1% by weight, of diagnostic additives, they contain at least as much additives as are required to enable the desired effect to be perceived. When the method according to the invention is used, diagnostic additives have to be applied to support materials in such a quantity that the desired effect can be perceived.

The following combinations of support material, diagnostic additives and treatment agents have proved to be of particular value:

Support materials preferably used are, for example, alginate impression materials provided with diagnostic additives which enable carious processes to be determined in a site-specific manner using a color signal. Support materials of this nature can, in a highly satisfactory manner, be provided with fluoride gels, such as Elmex jelly (from Wybert) at the stained site with the aim of achieving ultraprecise fluoridation in depth.

Another preferred combination is represented by alginate or polyether impression materials which contain diagnostic additives which enable periodontally infected gingival pockets to be stained in a site-specific manner. These support materials can be very readily provided, at the stained sites, with locally active antibiotics in the form of lacquers.

The treatment device can, for example, be prepared by aliquoting a support material, which contains diagnostic additives, into an impression spoon and using this latter to take a negative imprint of hard tissue. Infected sites in the hard tissue generate identifiable signals on the surface of the support material which faces the hard tissue.

A treatment agent is subsequently applied to these sites.

In another embodiment, the negative mold is used to generate a positive imprint which, for its part, is used as a model for producing an individual treatment device, preferably in the form of a mouthpiece, which can be used over a long period.

The materials which are known to the skilled person for producing individual mouthpieces or impression spoons are suitable for making such a mouthpiece.

Such an individual treatment device normally displays markedly superior wearability and can be used repeatedly independently of any visit to the dentist.

The regions which have been detected in the negative mold as being infected regions on the hard tissue are marked on the surface of the individual mouthpiece. A treatment agent can be applied repeatedly to these regions.

This is particularly advantageous when it appears necessary to treat the infected sites on the hard tissue over a relatively long period of time of, for example, several weeks.

In a preferred embodiment, the surface of the support material is pretreated at these sites, for example such that material is removed from these sites in order to create a reservoir for the treatment agent which is to be applied.

Depending on the treatment agent which is to be applied, it can also be advantageous to create a key before carrying out the application.

Such a key can, for example, be created by roughening the surface in this region. A primer-like substance can also be applied either in addition or as an alternative.

The invention is described in more detail below with the aid of examples.

APPLICATION EXAMPLE 1

Detecting Arg-Gingipain Using a Polyether Impression Material

A basal paste was prepared in an ordinary laboratory three-finger kneader by mixing 53.2 parts by weight of an aziridinopolyether, which was obtained as described in example 12 in DE-C-17 45 810, to homogeneity with 18.1 g of an hydrogenated palm oil and 6.4 parts by weight of dibenzyltoluene. This substance was combined with 11.8 parts of a copolymer composed of ethylene oxide and tetramethylene oxide units having an average molar mass of 6500 and also 0.1 parts of laurylimidazole and 5.0 parts of a block copolymer composed of ethylene oxide and propylene oxide units having an average molar mass of 3500. This substance was then mixed with 5.3 parts by weight of keiselguhr.

A catalyst paste was blended by homogenizing 33.8 parts by weight of acetyltributylcitrate with 14.1 parts of ethylene oxide-propylene oxide block copolymer and 19.0 parts of a sulfonium salt which was obtained as described in example 31 in DE-C-25 15 593. This substance was combined with 11 parts of kieselguhr and 205 parts of pyrogenic silicic acid and also 1 part of titanium dioxide. 0.7 g of tris(hydroxymethyl)aminomethane and 0.8 g of glycylglycine were then added as buffering substances, while 200 µg of N-t-Boc-Val-Pro-Arg-7-amido-4-methylcoumarin were added as substrate.

The basal paste and the catalyst paste were mixed in a ratio by volume of 5:1 and cured after approx. 8 minutes to give a homogeneous rubber. Doping the surface of this rubber during the setting phase with 2 µl of Art-gingipain-containing solution (stock solution: 0.5 mg of Arg-gingipain/ml in 200 mM tris(hydroxymethyl)aminomethane, pH 7.6) resulted, after a few minutes, in the appearance of an intensively blue fluorescent emission, at an excitation wavelength of 360 nm, at this site.

Following on from this, the labeled sites are painted with Elyzol Dentalgel (from Colgate, active compound, metronidazole benzoate).

APPLICATION EXAMPLE 2

Detecting Arg-Gingipain on Alginate Test Pieces 20 ml of a solution containing 0.12 g of tris(hydroxymethyl)aminomethane, 100 µg of N-t-Boc-Val-Pro-Arg-7-amido-4-methylcoumarin, pH 7.6, were added to 10 g of alginate (Palgat Plus Quick, from ESPE Dental AG) and the whole was kneaded to a homogeneous substance within 1 min using a broad plastic spatula. During the setting phase, the alginate test piece was doped with 2 µl of Arg-gingipain-containing solution (stock solution: 0.5 mg of Arg-gingipain/ml in 200 mM tris(hydroxymethyl)aminomethane, pH 7.6). After 5 min, it was possible to observe an intensively blue fluorescent emission, at an excitation wavelength of 360 nm, at this site.

Following on from this, the labeled sites are painted with Elyzol Dentalgel (from Colgate, active compound, metronidazole benzoate).

APPLICATION EXAMPLE 3

Detecting Arg-Gingipain in Gingival Pockets Using an Alginate Impression Material 40 ml of a solution containing 0.24 g of tris(hydroxymethyl)aminomethane, 0.26 g of glycylglycine and 200 µg of N-t-Boc-Val-Pro-Arg-7-amido-4-methylcoumarin were added to 20 g of alginate (Palgat Plus Quick, from ESPE Dental AG) and the whole was kneaded into a homogeneous substance within 1 min using a broad plastic spatula. The alginate substance was introduced into a commercially available impression spoon and positioned on the upper jaw or lower jaw of a periodontitis patient for 5 min. It was possible to observe intensively blue fluorescent emissions, at an excitation wavelength of 360 nm, at individual gingival pocket edges. Following on from this, the labeled sites are painted with Elyzol Dentalgel (from Colgate, active compound, metronidazole benzoate).

The cured impression material which has been prepared in this way is now repositioned in the mouth of the patient and left there for a period of approx. 10 minutes.

APPLICATION EXAMPLE 4

Detecting Lactic Acid on Alginate Test Pieces 10 ml of a solution containing 0.065 g of glycylglycine, 0.06 g of tri(hydroxymethyl)aminomethane, 9 mg of NAD, 0.23 mg of phenazine methosulfate, 0.75 mg of 3-(4,5-dimethyl-2-thiazolyl)-2,5-diphenyltetrazolium bromide (MTT) and 463 units of porcine heart lactate dehydrogenase were added to 5 g of alginate and the whole was kneaded into a homogeneous substance within 1 min using a broad spatula. The alginate test piece was doped with 5 µl of a 10 mM Ca lactate solution in 100 mM tris(hydroxymethyl)aminomethane, pH 9.0. After 4 min, it was possible to observe the development of a blue coloration at the doping site.

Following on from this, the stained sites are slightly excised with a scalpel and then filled with Elmex jelly (from Wybert).

APPLICATION EXAMPLE 5

Using an Alginate Impression Material to Determine the Formation of Lactic Acid on Teeth 40 ml of a solution containing 0.26 g of glycylglycine, 0.24 g of tri(hydroxymethyl)aminomethane, 36 mg of NAD, 0.9 mg of phenazine methosulfate, 3 mg of 3-(4,5-dimethyl-2-thiazolyl)-2,5-diphenyltetrazolium bromide (MTT) and 1850 units of porcine heart lactate dehydrogenase were added to 20 g of alginate and the whole was kneaded into a homogeneous substance within 1 min using a broad spatula. The alginate substance was introduced into a commercially available impression spoon and positioned on the upper jaw or lower jaw of a patient. The patient should have previously cleaned his teeth and rinsed them with a 1% sucrose solution. After 4 min, the impression spoon was removed. Sites at which lactic acid has been formed can be recognized by the blue coloration which develops.

Following on from this, the stained sites are excised slightly with a scalpel and then filled with Elmex jelly (from Wybert). The cured impression material which has been prepared in this way is now repositioned in the mouth of the patient and left there for a period of approx. 10 minutes.

The invention claimed is:

1. A method for treating intra-oral hard tissue infection in a site-specific manner, the method comprising the steps of:
   preparing an impression material that includes a diagnostic additive;
   applying the impression material to the intra-oral hard tissue to generate a negative mold of the hard tissue;
   generating an identifiable signal on the negative mold by the diagnostic additive at a location corresponding to an area of infected tissue on the intra-oral hard tissue;
   removing the negative mold from the intra-oral hard tissue;
   applying a treatment agent to the negative mold at the location corresponding to the area of infected tissue on the intra-oral hard tissue; and
   applying the negative mold on the intra-oral hard tissue such that the treatment agent is applied to the area of infected tissue on the intra-oral hard tissue.

2. The method according to claim 1, wherein the impression material is:
   based on silicone, polyether silicone, polyether, alginate or hydrocolloid,
   derived from polyethylenes, polypropylenes, poly(meth)acrylates, polyurethanes, polycarbonates, polysulfide, polyvinyl chlorides or rubber,
   a hydrogel based on polyvinylpyrrolidone or polyvinyi alcohol, or
   a dental gypsum preparation.

3. The method according to claim 1, wherein the diagnostic additive is present in microencapsulated form.

4. The method according to claim 1, wherein the diagnostic additive is a dye indicator, fluorescent indicator, chemoluminescent indicator, vital indicator, antibody, enzyme, or buffering substance.

5. The method according to claim 1, wherein the treatment agent is selected from the group consisting of a fluoridating agent, an antibiotic, a bacteriostatic, a quaternary ammonium compound and a mineral mixture which enables a hard tooth substance to be remineralized efficiently.

6. The method according to claim 1, wherein a surface of the negative mold is pretreated at the location where the treatment agent is applied.

7. The method according to claim 1, wherein the diagnostic additive is present in a quantity of from about 0.0001 to about 10% by weight.

8. The method according to claim 7, wherein the diagnostic additive is present in a quantity of from about 0.01 to about 1% by weight.

9. A method for preparing a treatment device, the method comprising the steps of:
   providing an impression material that includes a diagnostic additive which generates an identifiable signal on contact with infected intra-oral hard tissue,
   preparing a negative mold of the intra-oral hard tissue with the impression material, and
   applying a treatment agent to the negative mold at a location of an identifiable signal generated by the diaenostic additive.

10. A treatment device prepared according to the method of claim 9.

11. A method for producing an individual treatment device, comprising the steps of:
   preparing an impression material that includes a diagnostic additive which generates an identifiable signal on contact with infected tissue,
   applying the impression material to hard tissue to generate a negative mold of the hard tissue, preparing a positive mold using the negative mold,
preparing a mouthpiece using the positive mold, and
transferring to, or marking on, the mouthpiece a location on the negative mold of an identifiable signal generated by the diagnostic additive.

12. The method according to claim 11, further comprising the step of applying a treatment agent to the mouthpiece at the location.

* * * * *

UNITED STATES PATENT AND TRADEMARK OFFICE
CERTIFICATE OF CORRECTION

PATENT NO. : 7,147,471 B2
APPLICATION NO. : 10/433895
DATED : December 12, 2006
INVENTOR(S) : Oliver Frey It is certified that error appears in the above-identified patent and that said Letters Patent is hereby corrected as shown below:

On the Title Page, Item -56- under (Foreign Patent Documents)
Line 2, delete "17445810" and insert -- 1745810 --, therefor.

On the Title Page, Item -57- under (Abstract)
Line 11, delete "mouse piece" and insert -- mouthpiece --, therefor.

Column 4
Lines 4-5, delete "polymethanes," and insert -- polyurethanes, --, therefor.
Line 30, delete "DE-A-40 93 555," and insert -- U.S. Pat. No. 4,093,555, --, therefor.

Column 6
Lines 14-15, delete "(4-nitophenyl)" and insert -- (4-nitrophenyl) --, therefor.
Line 22, delete "-2 H-tetrazolium" and insert -- -2H-tetrazolium --, therefor.

Column 7
Lines 50-51, delete "(2-hydroxyethyl-piperazinyl)" and insert
    -- (2-hydroxyethyl-1-piperazinyl) --, therefor.

Column 9
Line 39, delete "fingi" and insert -- fungi --, therefor.

Column 11
Line 10, before "least" delete "at".
Line 46, delete "Na-benzoyl-DL-" and insert -- Nα-benzoyl-DL- --, therefor.

UNITED STATES PATENT AND TRADEMARK OFFICE
CERTIFICATE OF CORRECTION

PATENT NO.       : 7,147,471 B2                                    Page 2 of 2
APPLICATION NO.  : 10/433895
DATED            : December 12, 2006
INVENTOR(S)      : Oliver Frey It is certified that error appears in the above-identified patent and that said Letters Patent is hereby corrected as shown below:

Column 16
Line 26, in Claim 2, delete "polyvinyi" and insert -- polyvinyl --, therefor.
Line 58, in Claim 9, delete "diaenostic" and insert -- diagnostic --, therefor.

Signed and Sealed this

Third Day of June, 2008

JON W. DUDAS
*Director of the United States Patent and Trademark Office*